United States Patent [19]

Mimoun et al.

[11] 4,310,704

[45] Jan. 12, 1982

[54] PROCESS FOR MANUFACTURING METHYL KETONES BY OXIDATION OF TERMINAL OLEFINS

[75] Inventors: Hubert Mimoun, Rueil-Malmaison; Robert Charpentier, Villeneuve les Sablons; Michel Roussel, Colombes, all of France

[73] Assignee: Institut Francais du Petrole, Rueil-Malmaison, France

[21] Appl. No.: 104,941

[22] Filed: Dec. 18, 1979

[30] Foreign Application Priority Data

Dec. 18, 1978 [FR] France ................................ 78 35740
Jan. 11, 1979 [FR] France ................................ 79 00828
Nov. 13, 1979 [FR] France ................................ 79 28154

[51] Int. Cl.$^3$ ............................................. C07C 45/28
[52] U.S. Cl. .................................. 568/385; 568/342; 568/311; 252/429 R
[58] Field of Search .................. 260/597 B, 592; 252/429 R; 568/430, 420, 489, 401, 360, 320, 342, 365, 385, 408, 311

[56] References Cited

U.S. PATENT DOCUMENTS

| | | | |
|---|---|---|---|
| 3,122,586 | 2/1964 | Berndt et al. | 260/597 B |
| 3,231,620 | 1/1966 | Cotterill et al. | 260/597 B |
| 3,318,891 | 5/1967 | Hausman et al. | 260/597 B |
| 3,370,073 | 2/1968 | Clement et al. | 568/338 |
| 3,410,807 | 11/1968 | Lloyd | 252/429 R |
| 3,879,467 | 4/1975 | Zajacek et al. | 260/597 B |
| 3,927,111 | 12/1975 | Robinson | 260/597 B |
| 3,932,521 | 1/1976 | Gloyer et al. | 260/597 B |

OTHER PUBLICATIONS

Neckers et al., "Organic Chemistry", John Wiley & Son, pp. 1040-1042 (1977).
Cotton et al., "Adv. Inorg. Chem.", Interscience Publ., pp. 753-755 (1972).

Primary Examiner—G. T. Breitenstein
Assistant Examiner—James H. Reamer
Attorney, Agent, or Firm—Millen & White

[57] ABSTRACT

Methyl ketones are prepared in liquid phase by oxidizing terminal olefins of the formula R—CH=CH$_2$, where R is a hydrocarbon radical. The oxidizing agent is hydrogen peroxide or an organic hydroperoxide, and the catalyst is a palladium catalyst of the formula Pd AA', (L$_m$) where A is fluoborate, acetate or trefrafluoroacetate
A' is the same as A or is $\pi$-allyl,
m is 0 or 2, and
L is a ligand selected from the amines, the phosphines, the arsines, the stibines and the amides.

20 Claims, No Drawings

PROCESS FOR MANUFACTURING METHYL KETONES BY OXIDATION OF TERMINAL OLEFINS

BACKGROUND OF THE INVENTION

The present invention relates to a process for the selective manufacture of methyl ketones of the formula $$CH_3-\overset{O}{\underset{\|}{C}}-R$$

by oxidation, in liquid phase, of olefins of the formula $R-CH=CH_2$. R is alkyl, aryl, aralkyl or alkylaryl hydrocarbon radicals having each from 1 to 20 carbon atoms. Non-limitative examples thereof are propylene, 1-butene, terminal pentenes, hexenes, heptenes, octenes, decenes, dodecenes or styrene.

The method, according to the invention, for manufacturing methyl ketones consists of operating in the presence, on the one hand, of a specific palladium catalyst as defined below and, on the other hand, of an oxidizing agent which is either hydrogen peroxide or a carefully selected organic hydroperoxide.

In the known processes of the Wacker Type, wherein carbonyl compounds are synthesized from olefins, the catalytic system is usually formed of two associated metals, one of them being usually palladium, the other being usually copper or iron, the two metals being used as halides, particularly as chlorides. This catalytic system can be used with water which is the main source of the oxygen incorporated to the ketone.

These processes have however the disadvantage to operate in a very corrosive concentrated hydrochloric acid medium and to necessitate special alloys. Moreover, they are selective only for the oxidation of light olefins such as ethylene and propylene. The production of methylketones from heavier olefins usually results in the formation of undesirable chlorinated materials and aldehydes. Improvements have, however, been brought to the selectivity, when oxidizing heavy olefins, for example, by using organic solvents (French Pat. No. 1,564,635 or U.S. Pat. No. 3,410,807); however the disadvantages associated to the use of the bimetallic system are not avoided.

Other known processes are disclosed in the U.S. Pat. No. 3,932,521 and No. 3,370,073 concerning the oxidation of olefins in the presence of oxygen and a catalyst selected from the group consisting of palladium sulfate, the palladium halides, palladium phosphate and palladium acetate, or a Pd+HCl system. These processes are themselves not sufficiently selective, particularly when using palladium halides or hydrochloric acid.

DETAILED DISCUSSION

One of the advantages of the present process, according to the invention, is to operate in the complete absence of chloride ions, thus avoiding any risk of corrosion. Another advantage is to use a salt or complex of a single metal, palladium.

This process has the main advantage of being selective in the conversion to ketones, of olefins containing up to 20 carbon atoms per molecule, this selectivity being attributable to the choice, as catalyst, of a very specific palladium salt or complex which is used together with an oxidizing agent which is exclusively hydrogen peroxide or a particular organic hydroperoxide. When operating according to the invention, the selectivities are far better than with the use of Pd Cl₂ or Pd+HCl as catalyst system in the presence of hydrogen peroxide, as disclosed in the French Pat. No. 1,293,951 (U.S. Pat. No. 3,231,620).

It is to be noted that the U.S. Pat. No. 3,891,711 discloses the use of organic hydroperoxides for converting olefins to ketones in the presence of sulfurized palladium or platinum complexes. However these complexes have a low activity and they operate at high temperature. They have also a low selectivity.

The catalyst of the invention is a palladium salt or complex of the formula Pd AA', (L$_m$) where A and A' are usually identical or different anions. When identical, they are selected from the group consisting of a fluoborate, an acetate or a trifluoroacetate. When different, A is selected as above and A' may be selected from the group comprising the $\pi$-allyl radicals or the OOR$_1$ radicals where R$_1$ is a hydrocarbon radical preferably selected from the group consisting of a tertbutyl, an isopentyl and a cumyl radical; L is a ligand selected from the amines, phosphines, arsines, stibines or the amides such as diemthylformamide or hexamethylphosphoramide; m is zero or 2. Examples of catalyst to be used in the invention are: palladium acetate, palladium trifluoroacetate, palladium fluoborate or the following complexes:

Pd(CH₃CO₂)₂[P(C₆H₅)₃]₂
(CF₃CO₂)₂Pd[P(C₆H₅)₃]₂
CF₃CO₂Pd—O—O—C(CH₃)₃
CH₃CO₂Pd—O—O—C(CH₃)₃
Pd(CH₃CO₂)₂(HMPT)₂(HMPT:hexamethylphosphorotriamide)
Pd(CF₃CO₂)₂(HMPT)₂
(CH₃O₂)Pd-$\pi$-C₆H₁₁($\pi$-C₆H₁₁=1-methyl-3 ethyl-$\pi$-allyl)
(CF₃CO₂)Pd-$\pi$-C₆H₁₁

When the olefins are oxidized with hydrogen peroxide, it is possible to operate without solvent, hydrogen peroxide being however used as an aqueous solution containing, for example, 2 to 98% by weight of peroxide. An aqueous-organic biphasic system may also be used, the aqueous phase consisting of hydrogen peroxide in solution (for example 2 to 98% b.w. of hydrogen peroxide) and the organic phase usually comprising the olefin, the resultant ketone, the palladium catalyst and optionally an organic solvent. This solvent is preferably either a chlorinated solvent (for example chloroform, dichloromethane, dichloroethane, chlorobenzene or another chlorinated hydrocarbon) or an ester (for example ethyl acetate) or an aromatic solvent such as benzene, toluene or xylene, or an alcohol (for example tert-butyl alcohol, tert-amyl alcohol, dimethyl phenyl carbinol and ethylene glycol) or a monocarboxylic acid (for example acetic acid, propionic acid and butyric acid). The use of an organic solvent, and particularly the use of a solvent selected from those specifically listed above results in a substantial improvement of the reaction velocity. Operation in a biphasic system constitutes an advantage when the starting olefin and the resultant ketone are insoluble in the aqueous phase. In that case it is sufficient to decant and separate the two phases. The ketone, which is present in the organic phase, may then be recovered by distillation. The unreacted olefin, the solvent, when used, and the catalyst are then recycled, if desired, into the reaction zone. Finally it is also possible to operate in a monophasic system: a solvent is added to the medium and dissolves both the olefin and the hydrogen peroxide. This solvent is preferably an alcohol (for example methanol, ethanol, isopropanol or tert-butanol) or a cyclic ether (for example tetrahydrofuran or dioxane) or an amide (for example dimethylformamide or hexamethyl phosphoramide).

As a rule, the molar ratio $H_2O_2$/olefin is advantageously selected from 0.1 to 10 and preferably from 1.5 to 5.

The ratio olefin/catalyst by weight is preferably selected from 10 to 10,000 and particularly from 100 to 1,000.

The reaction temperature is usually from 0° to 130° C., particularly from 40° to 70° C.

When the oxidizing agent is an organic hydroperoxide and not hydrogen peroxide, the hydroperoxide is the source of the oxygen atom which is found in the ketone.

The organic hydroperoxide to be used in the present invention has the general formula $R_2OOH$ where $R_2$ is a tertiary alkyl, aralkyl or alkylaryl hydrocarbon group with 4 to 20 carbon atoms.

Non-limitative examples thereof are cumyl hydroperoxide, menthyl hydroperoxide and, most preferably, tert-butyl hydroperoxide. The reaction may be conducted in the absence of a solvent or in the presence of a solvent such as a chlorinated hydrocarbon, for example, dichloroethane, chlorobenzene or dichlorobenzene, an aromatic solvent such as benzene, toluene or xylene or a nitrogen-containing solvent such as nitrobenzene. The olefin/hydroperoxide molar ratio is usually from 0.1 to 10 and particularly from 0.1 to 0.5. The olefin/catalyst molar ratio is usually from 10 to 10,000 and particularly from 100 to 1,000.

The temperature is usually from 0° to 120° C., particularly from 20° to 80° C.

The invention is illustrated by the following non-limitative examples: (Examples 1 to 31 are conducted in the presence of hydrogen peroxide, and examples 31 to 41, in the presence of an organic hydroperoxide. The comparison example No. 42, is conducted in the presence of oxygen).

EXAMPLE 1

7.15 g of 1-octene, 18 g of ethyl acetate as organic solvent, 33 g of a 30% b.w. aqueous solution of hydrogen peroxide and 80 mg of palladium trifluoroacetate (0.28 m.moles) are introduced into a heat-insulated glass reactor. The resultant mixture is stirred at 60° C. by means of a magnetic stirrer. After 6 hours, 72% of 1-octene have been converted. The molar selectivity to 2-octanone is 90%.

EXAMPLE 2 (comparison)

Example 1 is repeated, except that the 0.28 m mole of palladium trifluoroacetate are replaced with 0.28 m mole of palladium chloride. After 6 hours, 75% of 1-octene have been converted. The molar selectivity to 2-octanone is 56%.

When replacing the 18 g of ethyl acetate with 15 ml of normal hydrochloric acid, it is found, after 6 l hours, that 79% of 1-octene have been converted, the molar selectivity to 2-octanone being 47%.

EXAMPLES 3 TO 10

These examples are effected as in example 1, however without ethyl acetate. 7.15 g of 1-octene, 11 g of a 30% aqueous solution of hydrogen peroxide and 0.24 millimole of a palladium salt or complex are introduced in the reactor. After 6 hours of reaction, the following results are obtained, when using various palladium complexes according to the invention.

| EXAMPLE No. | CATALYST | 1-Octene conversion % | MOLAR SELECTIVITY to 2-octanone |
|---|---|---|---|
| 3 | $Pd(CH_3CO_2)_2$ | 19 | 89 |
| 4 | $Pd(CF_3CO_2)_2$ | 19.5 | 90 |
| 5 | $CF_3CO_2$ Pd—O—O—$C(CH_3)_3$ | 16.6 | 82 |
| 6 | Palladium fluoborate | 16.3 | 81 |
| 7 | $CH_3CO_2$ Pd—O—O—$C(CH_3)_3$ | 16.5 | 82 |
| 8 | $Pd(CH_3CO_2)_2$ $(HMPT)_2$ | 19.2 | 88 |
| 9 | $(CF_3CO_2)$ Pd—$\pi$—$C_6H_{11}$ | 19.7 | 89 |
| 10 | $(CH_3CO_2)$ Pd—$\pi$—$C_6H_{11}$ | 19.1 | 89 |

EXAMPLES 11 TO 14 (comparison)

The operation is the same as in the examples 3 to 10, however with 0.24 millimole of palladium salt or complex which does not conform to the invention.

| EXAMPLE No. | CATALYST | 1-Octene conversion % | MOLAR SELECTIVITY to 2-octanone |
|---|---|---|---|
| 11 | $Pd Cl_2$ | 17.6 | 56 |
| 12 | $Pd SO_4$ | 8.5 | 63.1 |
| 13 | $Pd (NO_3)_2$ | 11.5 | 74 |
| 14 | $Pd (NO_3)_2(HMPT)_2$ | 12.9 | 75 |

EXAMPLES 15 TO 20

These examples show the influence of the presence and of the nature of various organic solvents on the velocity and selectivity of the reaction.

The operation is conducted in the same manner as in examples 3 to 10, in the optical presence of 10 cm$^3$ of chloroform or ethyl acetate (examples 15 and 18 are respectively identical to examples 4 and 3).

| EXAMPLE No. | SOLVENT | CATALYST | 1-Octene conversion % | MOLAR SELECTIVITY to 2-octanone % molar |
|---|---|---|---|---|
| 15 | (none) | $Pd (CF_3CO_2)_2$ | 19.5 | 90 |
| 16 | Ethyl acetate | " | 56 | 92 |
| 17 | Chloroform | " | 66 | 86 |
| 18 | (none) | $Pd (CH_3CO_2)_2$ | 19 | 89 |
| 19 | Ethyl acetate | " | 55 | 91 |
| 20 | Chloroform | " | 66 | 85 |

EXAMPLES 21 TO 26

These examples illustrate the reactivity of various olefins with respect to hydrogen peroxide in the presence of palladium catalysts.

The operation is the same as in example 1 at 60° C. by using 70 millimoles of olefin, with 80 mg of $Pd(CF_3CO_2)_2$ as catalyst and 18 g of ethyl acetate as solvent, using 33 g of a 30% aqueous solution of hydrogen peroxide.

The following Table illustrates the results obtained after 6 hours of reaction:

| EXAMPLE No | OLEFIN | CONVERSION % | RESULTANT PRODUCT | MOLAR SELECTIVITY % |
|---|---|---|---|---|
| 21 | 1-pentene | 80 | 2-pentanone | 95 |
| 22 | 1-hexene | 75 | 2-hexanone | 92 |
| 23 | 1-octene | 72 | 2-octanone | 92 |
| 24 | 1-decene | 60 | 2-decanone | 90 |
| 25 | 1-dodecene | 50 | 2-dodecanone | 85 |
| 26 | styrene | 52 | acetophenone | 88 |

EXAMPLE 27

20 g of ethyl acetate, 35 g of hydrogen peroxide and 100 mg of palladium trifluoroacetate are introduced into a stainless steel reactor. After heating to 60° C., 8 g of propylene is introduced under pressure and stirring is performed by means of a turbine. After 2 hours, acetone has formed with a molar selectivity of 95% for a propylene conversion of 90%.

EXAMPLE 28

The operation is as in example 27, however with 7 g of 1-butene. After 3 hours, methylethylketone forms with a molar selectivity of 94% for a conversion of 88%.

EXAMPLE 29

In a reactor of heat-insulated glass, there is introduced 66 g of 1-dodecene, 225 g of tert-butanol, 22.5 g of palladium acetate and then, dropwise under quick stirring, 55 g of a 70% b.w. aqueous solution of hydrogen peroxide. The temperature is then carefully raised to the reflux temperature (75° to 78° C.).

After 6 hours of reaction, 62% of 1-dodecene were converted. The molar selectivity to 2-decanone is 84.5%.

EXAMPLE 30

The operation is as in example 29, however with 33.6 g of 1-octene 176 g of tert-butanol as solvent, 45.5 mg of palladium acetate and 73 g of 70% hydrogen peroxide.

After 6 hours of reaction, 91.6% of 1-octene were converted. The molar selectivity to 2-octanone is 91%.

EXAMPLE 31

33.6 g of 1-octene, 236 g of 100% acetic acid as solvent and 45 mg of palladium acetate are introduced into a heat-insulated glass reactor. The mixture is stirred with a mechanical stirrer. 130 g of a 30% b.w. aqueous solution of hydrogen peroxide is added and the mixture is maintained at reflux (80° C.).

After 4 hours reaction, it is found that 96.7% of 1-octene were converted. The molar selectivity to 2-octanone is 94.8%.

EXAMPLE 32

30 cm³ of 80% tert-butyl hydroperoxide (0.225 mole), 10 cc of 1-hexene (0.064 mole), 20 cc of dichloroethane and 220 mg of palladium acetate (0.001 mole) are introduced into a heat-insulated glass reactor. An argon atmosphere is applied and stirring is performed at a temperature of 60° C. After 4 hours, it is found that 66% of 1-hexene were converted and that 2-hexanone was formed with a molar selectivity of 83% with respect to the converted 1-hexene.

EXAMPLES 33 TO 41

These examples illustrate the influence of the nature of the coordinates linked to the metal on the velocity and selectivity to 2-octanone from 1-octene. The technique is as in example 32 with the following conditions:

Catalyst: 0.1 mmole; 1-octene: 6.5 mmoles (1 cc); 80% tert-butyl hydroperoxide: 3 cc (23 mmoles). The solvent is toluene (2 cc); temperature: 50° C.; reaction time: 4 hours.

Only the catalysts of the examples 33, 34, 35 and 40 conform to the invention.

| EXAMPLE No. | CATALYST | 2-OCTANONE formed (millimole) | % MOLAR SELECTIVITY |
|---|---|---|---|
| 33 | Pd(CH$_3$CO$_2$)$_2$ | 3.5 | 75 |
| 34 | Pd(CF$_3$CO$_2$)$_2$ | 4.3 | 80 |
| 35 | (CF$_3$CO$_2$)Pd—$\pi$—C$_6$H$_{11}$ | 4.0 | 81 |
| 36 | Pd(acetylacetonate)$_2$ | 2.1 | 65 |
| 37 | Pd Cl$_2$(C$_6$H$_5$CN)$_2$ | 0.4 | 30 |
| 38 | Pd((C$_2$H$_5$)$_2$ NCS$_2$)$_2$ | 0.02 | — |
| 39 | Pd[S$_2$C$_2$(C$_6$H$_5$)$_2$]$_2$ | 0.04 | — |
| 40 | CH$_3$CO$_2$Pd—O—O—C(CH$_3$)$_3$ | 3.6 | 76 |
| 41 | Pd[P(C$_6$H$_5$)$_3$]$_4$ | 2.2 | 60 |

These examples show that the catalysts which do not conform to the invention, and particularly the chlorine and sulfur compounds, have a strongly inhibiting effect on the velocity and selectivity of the reaction.

EXAMPLE 42

Example 1 is repeated, however without hydrogen peroxide. The reactor is now connected to a source of pure oxygen at a pressure of 1.1 bar. The oxygen consumption is read on a manometer in the course of time, and gas phase chromatography is used to follow up the formed 2-octanone and the consumed 1-octene. After 65 minutes, it is found that 1-octene has disappeared completely and that 2-octanone has been formed with a molar selectivity of only 38%.

What is claimed is:

1. A process for producing a methyl ketone of the formula

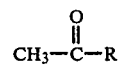

from an olefin of the formula CH$_2$=CHR wherein R is C$_{1-20}$ hydrocarbyl, said process comprising the step consisting essentially of contacting said olefin in the liquid phase, optionally in the presence of a solvent, with a palladium catalyst and a peroxide oxidizing agent;

wherein said palladium catalyst has the formula PdAA'(L)$_m$, wherein A is fluoborate, acetate or trifluoroacetate; A' is the same as A or a $\pi$-allyl radical; L is an amine, phosphine, arsine, stibine or amide ligand; and m is 0 or 2; and wherein said oxidizing agent is hydrogen peroxide or an organic hydroperoxide of the formula R$_2$OOH, wherein R$_2$ is C$_{4-20}$ tertiary alkyl, aralkyl or alkylaryl.

2. A process according to claim 1, wherein the catalyst is one of palladium acetate, palladium trifluoracetate, palladium fluoborate or a complex of the formula:

Pd(CH$_3$CO$_2$)$_2$[P(C$_6$H$_5$)$_3$]$_2$
(CF$_3$CO$_2$)$_2$Pd[P(C$_6$H$_5$)$_3$]$_2$
CF$_3$CO$_2$Pd—O—O—C(CH$_3$)$_3$
CH$_3$CO$_2$Pd—O—O—C(CH$_3$)$_3$
Pd(CH$_3$CO$_2$)$_2$(HMPT)$_2$
Pd(CF$_3$CO$_2$)$_2$(HMPT)$_2$
(CH$_3$CO$_2$)Pd-$\pi$-C$_6$H$_{11}$
(CF$_3$CO$_2$)Pd-$\pi$-C$_6$H$_{11}$.

3. A process according to claim 2, wherein said oxidizing agent is hydrogen peroxide, the molar ratio H$_2$O$_2$/olefin being from 0.1 to 10, and the ratio by weight olefin/catalyst being from 10 to 10,000.

4. A process according to claim 3, wherein the molar ratio H$_2$O$_2$/olefin is from 1.5 to 5, the ratio by weight olefin/catalyst being from 100 to 1,000.

5. A process according to claim 4, wherein hydrogen peroxide is used in aqueous solution.

6. A process according to claim 5, wherein the olefin is further diluted in an organic solvent, said solvent being a chlorinated hydrocarbon, an ester, an aromatic solvent, an alcohol, or a monocarboxylic acid.

7. A process according to claim 6, wherein the solvent is chloroform, ethyl acetate, tert-butyl alcohol, or acetic acid.

8. A process according to claim 4, wherein the hydrogen peroxide and the olefin are dissolved in an organic solvent, said solvent being an alcohol, a cyclic ether, or an amide.

9. A process according to claim 2, wherein said oxidizing agent is tert-butyl or cumyl hydroperoxide, the molar ratio olefin/hydroperoxide being from 0.1 to 10 and the molar ratio olefin/catalyst being from 10 to 10,000.

10. A process according to claim 9, wherein the molar ratio olefin/hydroperoxide is from 0.1 to 0.5, the molar ratio olefin/catalyst being from 100 to 1,000.

11. A process according to claim 1, wherein in said catalyst, the $\pi$-allyl radical is a 1-methyl-3-ethyl-$\pi$-allyl radical; and L is one of triphenylphosphine, dimethylformamide and hexamethylphosphoramide.

12. A process according to claim 1, wherein said step is effected in the absence of chloride ions.

13. A process according to claim 1, wherein the catalyst is one of palladium acetate, palladium trifluoroacetate palladium fluoborate or a complex of the formula:
Pd(CH$_3$CO$_2$)$_2$[P(C$_6$H$_5$)$_3$]$_2$
(CF$_3$CO$_2$)$_2$Pd[P(C$_6$H$_5$)$_3$]$_2$
Pd(CH$_3$CO$_2$)$_2$(HMPT)$_2$
Pd(CF$_3$CO$_2$)$_2$(HMPT)$_2$
(CH$_3$CO$_2$)Pd-$\pi$-C$_6$H$_{11}$
(CF$_3$CO$_2$)Pd-$\pi$-C$_6$H$_{11}$.

14. A process according to claim 3, wherein said step is effected at a temperature of from 0° to 130° C.

15. A process according to claim 4, wherein said step is effected at a temperature of from 40° to 70° C.

16. A process according to claim 8, wherein said organic solvent is methanol, ethanol, isopropanol, tert.-butanol, tetrahydrofuran dioxane, dimethylformamide, or hexamethylphosphoramide.

17. A process according to claim 9, wherein said step is effected at a temperature of from 0° to 120° C.

18. A process according to claim 10, wherein said step is effected at a temperature of from 20° to 80° C.

19. A process according to claim 10, wherein said step is effected in the presence of a solvent, said solvent being a chlorinated hydrocarbon, an aromatic solvent, or a nitrogen-containing solvent.

20. A process according to claim 19, wherein said solvent is dichloroethane, chlorobenzene, dichlorobenzene, benzene, toluene, xylene, or nitrobenzene.

* * * * *